US012023231B2

(12) United States Patent
Liu

(10) Patent No.: US 12,023,231 B2
(45) Date of Patent: Jul. 2, 2024

(54) METHOD AND APPARATUS FOR PRODUCING FILLER-CONTAINING SUBSTRATE, AND SUBSTRATE PRODUCED USING METHOD

(71) Applicant: Wanxiang Liu, Pudong New District Shanghai (CN)

(72) Inventor: Wanxiang Liu, Pudong New District Shanghai (CN)

(73) Assignee: JOFO New Material Co., Ltd., Shandong (CN)

( * ) Notice: Subject to any disclaimer, the term of this patent is extended or adjusted under 35 U.S.C. 154(b) by 1111 days.

(21) Appl. No.: 16/469,130

(22) PCT Filed: Dec. 13, 2016

(86) PCT No.: PCT/CN2016/109595
§ 371 (c)(1),
(2) Date: Sep. 11, 2019

(87) PCT Pub. No.: WO2018/107349
PCT Pub. Date: Jun. 21, 2018

(65) Prior Publication Data
US 2020/0093655 A1 Mar. 26, 2020

(51) Int. Cl.
*A61F 13/53* (2006.01)
*A61F 13/15* (2006.01)
*B32B 27/04* (2006.01)

(52) U.S. Cl.
CPC ........ *A61F 13/53* (2013.01); *A61F 13/15739* (2013.01); *B32B 27/04* (2013.01)

(58) Field of Classification Search
CPC ..... A61F 13/53; A61F 13/15739; B32B 27/04
(Continued)

(56) References Cited

U.S. PATENT DOCUMENTS 2,619,441 A * 11/1952 Levy .................... D06N 3/0086
428/96
2,910,040 A * 10/1959 Agahd ................... D21H 25/10
118/120
(Continued)

FOREIGN PATENT DOCUMENTS

CN 101636133 A * 1/2010
JP H06341044 A * 12/1994
(Continued)

OTHER PUBLICATIONS

English machine translation of JPH06341044A; Takahata; Dec. 13, 1994; 5 pages. (Year: 1994).*
(Continued)

*Primary Examiner* — Linda L Gray
(74) *Attorney, Agent, or Firm* — Snell & Wilmer L.L.P.

(57) ABSTRACT

A method and an apparatus for producing a filler-containing substrate, as well as a substrate produced using the method, are disclosed. The substrate comprises a filler layer (201, 52, 801) and a seal layer (203, 51, 802). The method comprises: (a) forming holes in the filler layer (201, 52, 801); (b) spreading fillers on a porous surface of the filler layer (201, 52, 801) that has undergone hole formation; (c) horizontally shaking the filler layer (201, 52, 801) having the fillers spread thereon so as to allow the fillers to enter the holes; and (d) sealing the filler layer (201, 52, 801) having the holes containing the fillers so as to obtain the substrate. The apparatus comprises: a hole-forming device (21, 71) for forming the holes in the filler layer (201, 52, 801); a spreading device (23, 72) for spreading the fillers on the surface formed with the holes of the filler layer (201, 52, 801) that has undergone hole formation; a horizontal shaking device (24, 73) for horizontally shaking the filler layer (201, 52, 801) having the fillers spread thereon so as to allow (Continued)

the fillers to enter the holes; and a sealing device (25, 74, 312) for sealing the filler layer (201, 52, 801) having the holes containing the fillers.

12 Claims, 8 Drawing Sheets

(58) Field of Classification Search
USPC .................................. 156/153, 276; 118/120
See application file for complete search history.

(56) References Cited

U.S. PATENT DOCUMENTS

| | | | | |
|---|---|---|---|---|
| 3,205,116 | A | * | 9/1965 | Walsh .................. D06N 7/0013 425/363 |
| 6,660,326 | B2 | * | 12/2003 | Sano ........................ B05D 5/02 427/427 |
| 8,042,696 | B2 | * | 10/2011 | Olsta ........................ D04H 3/00 156/260 |
| 2016/0136683 | A1 | | 5/2016 | Pinyayev et al. |

FOREIGN PATENT DOCUMENTS

| | | |
|---|---|---|
| JP | 2002035036 A | 2/2002 |
| JP | 2011000231 A | 1/2011 |
| JP | 2014200252 A | 10/2014 |
| WO | WO2010061228 A1 * | 6/2010 ......... A61F 13/0253 |

OTHER PUBLICATIONS

English machine translation of CN101636133A; Noda; Jan. 27, 2010; 25 pages. (Year: 2010).*

* cited by examiner

METHOD AND APPARATUS FOR PRODUCING FILLER-CONTAINING SUBSTRATE, AND SUBSTRATE PRODUCED USING METHOD

CROSS-REFERENCE TO RELATED APPLICATIONS

This application is a U.S. National Phase filing under 35 U.S.C. § 371 of PCT Application Serial No. PCT/CN2016/109595 filed on Dec. 13, 2016, entitled METHOD AND APPARATUS FOR PRODUCING FILLER-CONTAINING SUBSTRATE, AND SUBSTRATE PRODUCED USING METHOD; the contents of the respective application is incorporated herein by reference in its entirety.

TECHNICAL FIELD

The present invention relates to a method and an apparatus for producing a filler-containing substrate, as well as a substrate produced using the method, and specifically discloses a method and an apparatus for producing a substrate that may enable dense distribution of fillers in the substrate and make the fillers to be vertical to the substrate in form of column, as well as a substrate produced using the method.

BACKGROUND

The core made of water absorbing resin as fillers is widely used for diapers to absorb and store urine.

The common structure of core is direct mixture of water absorbing resin and wood fibre, but due to the loose nature of wood fibre, water absorbing resin may swell when it is in contact with liquid, thereby causing the core to crepe, agglomerate or break.

Another prior art technique is to uniformly distribute and sandwich granular objects between two thin substrates. Alternatively, three layers of substrates are used to sandwich two layers of granular objects, and the intermediate layer is selected as fluffy substrate. On the basis of this, there is also an improved prior art in which streaks are pressed on the surface to form granular objects into block shapes on the basis of the technique mentioned above. However, the problem of optimal distribution of granular objects cannot be completely solved by the prior art techniques.

The problem of optimal distribution of granular objects actually consists of two levels:
 (a) Maximizing the sum of the surface areas of the shape formed by the granular object in the product, that is, the optimal state of the granular objects formed in the product is in small shape and large amount. Besides, the granular objects may not be blocked by themselves. However, in the prior art, when two or more layers are selected, the performance of the underlying granular objects tends to be affected by the upper granular objects.
 (b) Fixability of the granular objects in product. In particular, when the granular objects are water absorbers, whether the granular objects can be fixed in product after expansion caused by water absorption, or not.

For example, the invention patent application with the publication number CN101797201A discloses a polymer composite core and a producing method thereof, relating to a polymer composite core and a producing method thereof. The polymer composite core is provided with a dust-free paper surface layer, a dust-free paper bottom layer and a fluffy non-woven fabric layer, wherein the fluffy non-woven fabric layer is provided between the dust-free paper surface layer and the dust-free paper bottom layer, glued to the dust-free paper surface layer and the dust-free paper bottom layer by adhesive, and water absorbing resins are uniformly impregnated in the fluffy non-woven fabric layer. This patent application directly mixes water absorbing resins with fluffy non-woven fabric layer, and only discloses that the surface layer and the bottom layer are directly glued using an adhesive method. The following problems may exist in such a structure:
 (a) Most water absorbing resins may not effectively penetrate into the fluffy non-woven fabric layer and may stay between the fluffy non-woven fabric layer and the dust-free paper surface layer. Conflicts may occur when gluing with adhesive. Delamination may occur when there are many water absorbing resins and few adhesives. When there are few water absorbing resins and many adhesives, the adhesive therein will inhibit performance of the water absorbing resins.
 (b) Since water absorbing resins are uniformly densely sandwiched between fluffy non-woven fabric layer and dust-free paper surface layer, water absorbing resins may expand to form a barrier layer when in contact with liquid, which may structurally prevent further penetration of liquid. In particular, in structure of two or more layers, water absorbing resin of upper layer may directly affect performance of water absorbing resin of underlying layer.

SUMMARY

The present invention provides a method and an apparatus for producing filler-containing substrate, and substrate produced using the method, overcoming problems in prior art, increasing filling amount of fillers, meanwhile, enabling reasonable distribution of fillers in the substrate and making the fillers to be vertical to the substrate in form of column.

According to the object mentioned above, the present invention provides a method for producing filler-containing substrate comprising a filler layer and a seal layer, wherein the method comprises: (a) forming holes in the filler layer; (b) spreading fillers on a porous surface of the filler layer that has undergone hole formation; (c) horizontally shaking the filler layer having the fillers spread thereon so as to allow the fillers to enter the holes; and (d) sealing the filler layer having the holes containing the fillers so as to obtain the substrate.

In an embodiment, the formed holes are blind holes.

In an embodiment, the substrate further comprises a bottom layer, the formed holes are through holes, step (a) further comprises: (a1) bonding the bottom layer with one of the surfaces of the filler layer that has undergone hole formation to cover one of the openings of the through holes.

In an embodiment, step (d) comprises: (d1) gluing the seal layer to the surface with formed holes of the filler layer.

In an embodiment, step (d1) comprises: spraying glue on one of the surfaces of the seal layer; pressing the surface sprayed with glue of the seal layer against the surface with formed holes of the filler layer.

In an embodiment, step (a1) comprises: spraying glue on one of the surfaces of the bottom layer; pressing the surface sprayed with glue of the bottom layer against the surface with formed holes of the filler layer.

In an embodiment, step (d) comprises: removing the fillers in a plurality of separate strip regions on the filler layer that has undergone horizontal shake, wherein the strip regions are distributed along the length direction of the filler layer, and the strip regions are parallel to each other; gluing the seal layer to the surface with formed holes of the filler layer that has undergone filler removal to form a bonding layer of the seal layer and the filler layer; slitting the bonding layer along the strip regions so as to fuse incision of the bonding layer closed to obtain the substrate.

In an embodiment, the step of slitting comprises: slitting with heating slitting method or ultrasonic slitting method.

Corresponding to the method mentioned above, the present invention also provides an apparatus for producing filler-containing substrate comprising a filler layer and a seal layer, wherein the apparatus comprises: a hole-forming device for forming holes in the filler layer; a spreading device for spreading fillers on the surface formed with the holes of the filler layer that has undergone hole formation; a horizontal shaking device for horizontally shaking the filler layer having the fillers spread thereon so as to allow the fillers to enter the holes; and a sealing device for sealing the filler layer having the holes containing the fillers.

In an embodiment, the substrate further comprises a bottom layer, the holes are through holes, the hole-forming device comprises: a needle roller and a concave roller, wherein surface of the needle roller has needle protrusions; a heating mechanism for heating the needle roller and the concave roller to 90-250 degrees Celsius; surface of the concave roller has depressions matching the needle protrusions, the filler layer is placed between the needle roller and the concave roller, when the needle protrusions move into the depressions, the through holes are formed on the filler layer; and a bottom layer sealing device for bonding the bottom layer with one of the surface of the filler layer that has undergone hole formation to cover one of the openings of the through holes.

In an embodiment, the holes are blind holes, the hole-forming device comprises: a convex roller and a flat roller, wherein surface of the convex roller has flat head protrusions; a heating mechanism for heating the convex roller and the flat roller to 90-250 degrees Celsius; the filler layer is placed between the heated convex roller and the heated flat roller, when the flat head protrusions move to the flat roller, the blind holes are formed on the filler layer.

In an embodiment, the sealing device comprises: a glue spraying mechanism for spraying glue on one of the surfaces of the seal layer; a gluing mechanism for pressing the surface sprayed with glue of the seal layer against the surface with formed holes of the filler layer.

In an embodiment, the apparatus further comprises: at least two horizontal flattening rollers for holding the filler layer; a power device for powering the filler layer such that the filler layer is continuously movable along the length direction of the filler layer on the horizontal flattening rollers.

In an embodiment, the horizontal shaking device comprises: a first round roller and a second round roller, wherein the first round roller and the second round roller are tangent, and the filler layer that has filled by the fillers is clamped at the tangent, width of the first round roller and the second round roller is greater than width of the filler layer, the first round roller and the second round roller perform a linear reciprocating motion along the width direction of the filler layer at same frequency and amplitude.

In an embodiment, the sealing device comprises: a first round roller and a second round roller, wherein the first round roller and the second round roller are tangent, and the filler layer that has undergone horizontal shake is clamped at the tangent; a glue spraying mechanism for spraying glue on a surface of the seal layer; the first round roller performs a circular motion to drive the seal layer that has sprayed with glue, making the surface sprayed with glue of the seal layer contact the filler layer at the tangent, the second round roller performs a circular motion and presses the seal layer closed at the tangent to make the filler layer and the seal layer glued.

In an embodiment, the sealing device comprises: an absorbing mechanism, comprising a plurality of absorbing sub-mechanisms that are separate and parallel distributed, wherein opening of the absorbing sub-mechanism has a rectangular cross section, width of the rectangle is smaller than width of the filler layer, bottom of front end of the opening is curved, rear end is straight and close to the filler layer that has undergone horizontal shake, a negative pressure is generated in the rear end region, the absorbing mechanism is configured to remove the fillers in a plurality of separate strip regions on the filler layer that has undergone horizontal shake, the strip regions are distributed along the length direction of the filler layer, the strip regions are parallel to each other; a first round roller and a second round roller, wherein the first round roller and the second round roller are tangent, and the filler layer that has undergone filler absorption in the strip regions is clamped at the tangent; a glue spraying mechanism for spraying glue on a surface of the seal layer; the first round roller performs a circular motion to drive the seal layer that has sprayed with glue, making the surface sprayed with glue of the seal layer contact the surface formed with the holes of the filler layer at the tangent, the second round roller performs a circular motion and presses the seal layer closed at the tangent so as to make the filler layer and the seal layer glued to obtain a bonding layer of the seal layer and the filler layer; a slitting mechanism for slitting the bonding layer along the strip regions so as to fuse incision of the bonding layer closed to obtain the substrate.

In an embodiment, the slitting mechanism comprises: a heat knife, using heating method for slitting; or an ultrasonic knife, using ultrasonic method for slitting.

In an embodiment, the amplitude is 3-60 mm, the frequency $F=(K*V)/(30*L)$, which is in unit of hertz, the K is a frequency coefficient in a range from 3 to 20, the V is moving speed of the filler layer on the horizontal flattening roller in unit of m/min, the L is distance between the spreading mechanism and the sealing device in unit of meter, the L is 1-5 times the width of the filler layer.

In an embodiment, value of the K ranges from 3 to 5.

In an embodiment, value of the K ranges from 10 to 20.

The present invention also provides a substrate produced using the method mentioned above, comprising a filler layer and a seal layer, wherein blind holes are formed in the filler layer, the seal layer is sealingly bonded to the filler layer on surface formed with blind holes of the filler layer, the blind holes are filled with fillers.

In an embodiment, the substrate comprises a filler layer, a bottom layer and a seal layer, wherein through holes are formed in the filler layer, the seal layer and the bottom layer are respectively sealingly bonded to the filler layer on both sides of the filler layer, the through holes are filled with fillers.

In an embodiment, the filler is a water absorber, a water retainer, a topical drug, a disinfectant, an insecticide, a pesticide or a fertilizer.

As described above, the present invention provides a method for producing filler-containing substrate, which makes the fillers to fully penetrate into the formed holes by forming holes, spreading the fillers, shaking the fillers, and sealing the substrate, thereby further improving the using efficiency of the substrate.

Figure 1:
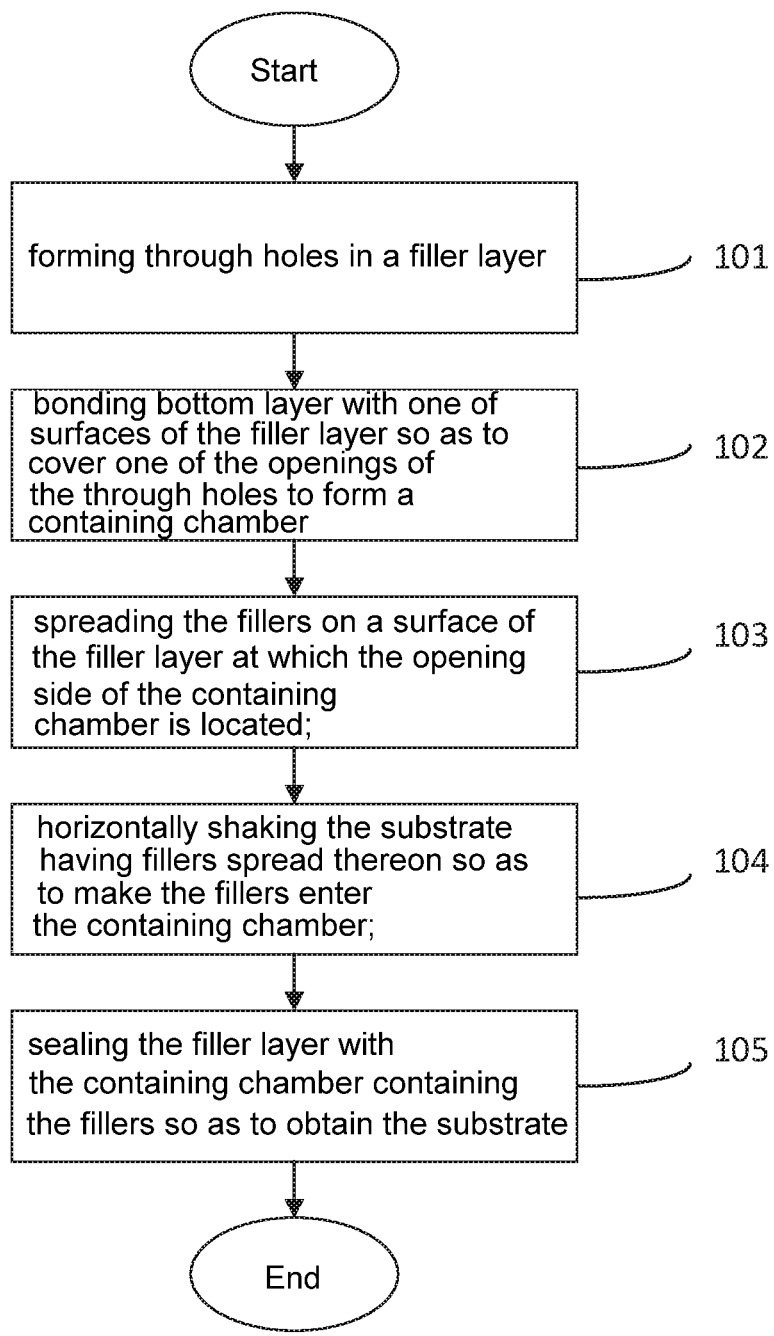
FIG. 1 shows a flow chart of an embodiment of producing method of the present invention.

For the sake of clarity, a brief description of reference signs is given below:

21, 71: hole-forming device
22: bottom layer sealing device
23, 72: spreading device
24, 73: horizontal shaking device
25, 74, 312: sealing device
201, 52, 801: filler layer
202, 53: bottom layer
203, 51, 802: seal layer
211: needle roller
212: concave roller
213: needle protrusions
214: depressions
215: filler layer formed with through holes
216: containing chamber (hole)
217: substrate filled with fillers in containing chambers (holes)
221, 251: glue spraying mechanism
222, 252: gluing mechanism
2221, 2521: first round roller of gluing mechanism
2222, 2522: second round roller of gluing mechanism
241: first round roller of horizontal shaking device
242: second round roller of horizontal shaking device
300: sealing device with absorbing mechanism
311: absorbing sub-mechanism
313: slitting mechanism
41: curved shape
42: rear end
43: negative pressure absorbing region
54: through hole
803: blind hole
804: surface formed with blind holes

DETAILED DESCRIPTION OF EMBODIMENTS

The present invention provides a method for producing filler-containing substrate. Referring to FIG. 1, FIG. 1 shows a flow chart of an embodiment of producing method of the present invention, wherein the method comprises:

101: forming through holes in a filler layer;
102: bonding bottom layer with one of surfaces of the filler layer so as to cover one of the openings of the through holes to form a containing chamber (hole);
103: spreading the fillers on a surface of the filler layer at which the opening side of the containing chamber (hole) is located;
104: horizontally shaking the substrate having fillers spread thereon so as to make the fillers enter the containing chamber (hole);
105: sealing the filler layer with the containing chamber (hole) containing the fillers so as to obtain the substrate.

The through holes provided in step 101 may be holes penetrating the filler layer. In order to fill the holes with the fillers and store the fillers in the holes, step 102 may be performed to bond the bottom layer with one of surfaces of the filler layer, so that a containing chamber (hole) may be formed by the through holes. In step 103, the fillers may be sprayed on a surface of the filler layer at which the opening side of the containing chamber (hole) is located, wherein the fillers may be uniformly distributed on the surface, some of which may enter the containing chamber (hole), and some other of which may be distributed in region of the surface without holes. The horizontally shaking operation of step 104 may be performed to shake the fillers that failed to enter the containing chamber (hole) to make them enter the containing chamber (hole). Finally, the containing chamber (hole) may be sealed in step 105. The fillers may thereby be distributed in the substrate.

According to the prior art, there are many methods that can form through holes on a substrate, and any one of them may be used for the perforation. Similarly, there are many ways to bond the bottom layer to the filler layer. In an embodiment, one of surfaces of the bottom layer may be sprayed with glue, and the bottom layer may be glued onto the filler layer by press bonding.

Subsequently, the filler may be spread onto the filler layer, wherein the filler may be a water absorber, a water retainer, an anti-inflammatory drug, a disinfectant, an insecticide, a pesticide or a fertilizer.

When sealing the substrate having containing chamber (hole) which contains fillers, same bonding method as that bonding the bottom layer may be selected.

In practical applications, width of the substrates are mostly small, such as diapers, sanitary napkins, etc., in which case the substrates need to be slit to form substrates of required size for use.

In an embodiment, the fillers in a plurality of separate strip regions on the filler layer that has undergone horizontal shake may be firstly removed, wherein the strip regions are distributed along the length direction of the filler layer, the strip regions are parallel to each other, and width of the strip regions are generally in range of 5-25 mm.

The purpose of removing the fillers is to pre-treat the substrate for slitting by a hot knife or an ultrasonic knife. The hot knife is used to heat the material to be bonded, so that the material may reach a viscous flow state and then pressurized to be slit. Since the material is in the viscous state at the time of slitting, the incision may be sealed and bonded after slitting. Since the fillers are generally made of polymer material, which is difficult to achieve a viscous flow state, the pre-treatment of previous filler suction is particularly necessary for better sealing the incision. The ultrasonic knife may apply the mechanical vibration of ultrasonic wave to the part to be slit. The part to be slit may vibrate and friction to generate heat so that the material of the part to be slit may melt, and may slit by pressurization. Similar to the principle of hot knife slitting, since the material of the slitting portion is melted at the time of slitting, the incision may also be sealed and bonded after slitting. Similarly, when slitting with an ultrasonic knife, previous filler suction at the incision is also need. When slitting the substrate by a hot knife or an ultrasonic knife, the substrate may not only be separated according to the actual use size, but also be sealed directly after the slit. Since the fillers at the incision has been sucked out before the slitting and the slitting is performed by a heating slitting method or an ultrasonic slitting method, incision of the substrate may be fused and sealed, thereby effectively preventing fillers from seeping out from incision at the slit surface.

Figure 2:
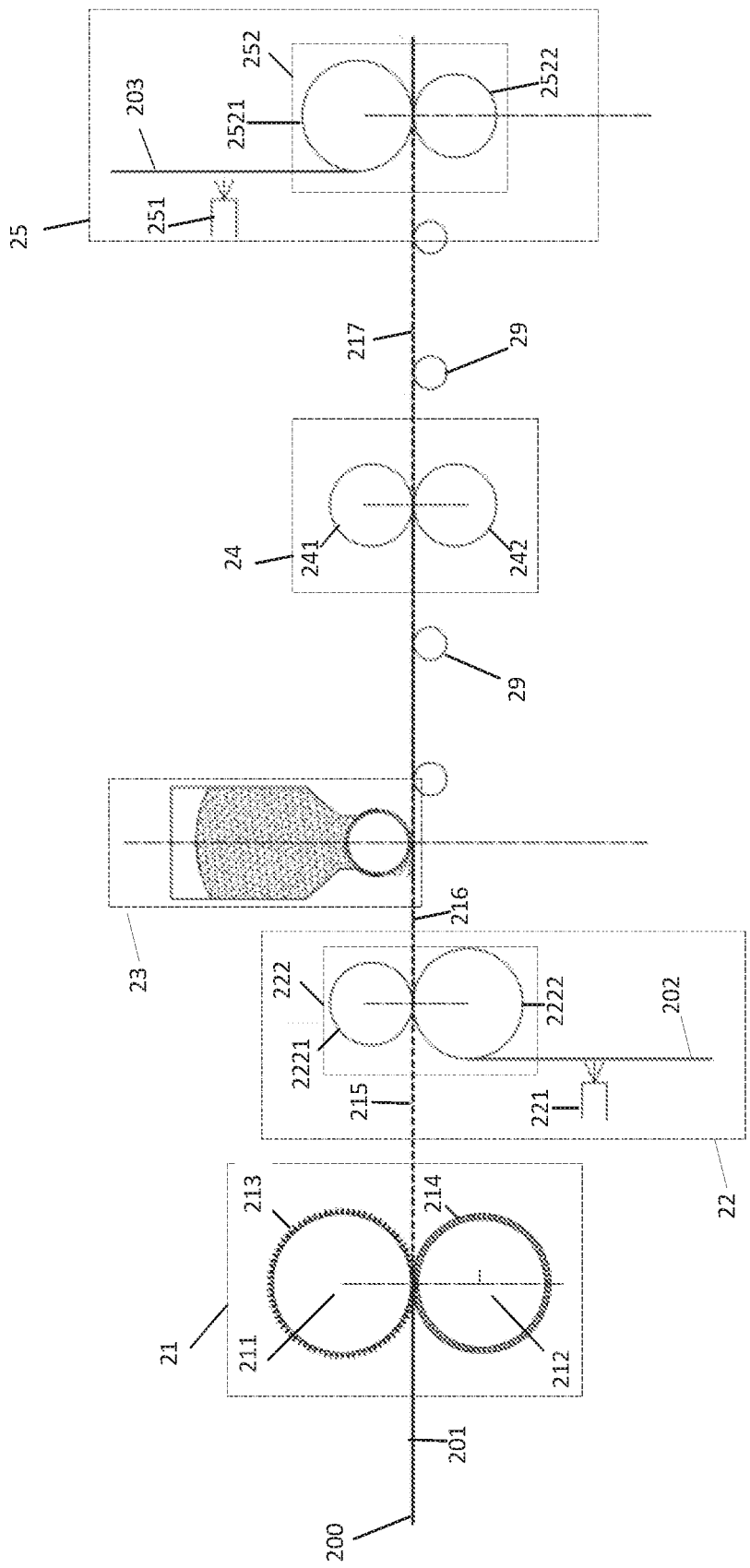
FIG. 2 shows a structure diagram of an embodiment of producing apparatus of the present invention.

Corresponding to the method mentioned above, the present invention also provides an apparatus for producing filler-containing substrate. Referring to FIG. 2, FIG. 2 shows a structure diagram of an embodiment of producing apparatus of the present invention, wherein the apparatus comprises:

a hole-forming device 21 for forming through holes in a filler layer;

a bottom layer sealing device 22 for bonding bottom layer with one of the surfaces of the filler layer so as to cover one of the openings of the through holes to form a containing chamber (hole);

a spreading device 23 for spreading the fillers on a surface of the filler layer at which the opening side of the containing chamber (hole) is located;

a horizontal shaking device 24 for horizontally shaking the substrate having fillers spread thereon so as to make the fillers enter the containing chamber (hole);

a sealing device 25 for sealing the filler layer with the containing chamber (hole) containing the fillers so as to obtain the substrate.

The hole-forming device 21 is used to form through holes in the filler layer, wherein the holes may be formed by a plurality of hole-forming devices in prior art. In an embodiment, the hole-forming device 21 may comprise a needle roller 211, a concave roller 212 and a heating mechanism, wherein needle protrusions 213 may be disposed on surface of the needle roller 211. For the sake of concision and clarity of the structure diagram, the heating mechanism is not shown in FIG. 2. The heating mechanism may heat the needle roller 211 and the concave roller 212 to a temperature of 90-250 degrees Celsius. Depressions 214 matching needle protrusions 213 of the needle roller 211 may be disposed on surface of the concave roller 212. The filler layer may be placed between the needle roller 211 and the concave roller 212. Since the needle roller 211 and the concave roller 212 have been heated, when the needle protrusions 213 are moved into the depressions 214, through holes may be made on the filler layer 201.

More preferably, the apparatus may further comprise at least two horizontal flattening rollers 29 for holding the producing material 200. Since the producing process in the embodiment is a continuous streamlined producing process, intermediate product of substrate production may probably be held by the horizontal flattening rollers. The filler layer may be held before and after hole formation. After gluing the bottom layer, composite structure material of the filler layer glued with the bottom layer may be held. After sealing upper layer to the filler layer, the finished substrate may be held.

The mentioned apparatus further comprises a power device for providing power to the substrate 201, so as to enable the substrate 201 to continuously move along the length direction of the substrate 201 on the horizontal flattening rollers 29, thereby making the entire producing process continuous. In the embodiment, the needle roller 211 is preferably a round roller, the concave portion 212 is preferably a round roller, and the needle roller 211 and the concave roller 212 may be tangent at their outer surface, sandwiching the substrate 201 at the tangent. When the filler layer moves, the needle roller and the concave roller make circular motions about their respective centres, and form through holes in the filler layer.

In another preferred embodiment, the bottom layer sealing device 22 is used to bond the bottom layer 202 with one of surfaces of the filler layer, so as to cover one of the openings of the through holes 215 to form a containing chamber (hole) 216. The bottom layer sealing device 22 comprises a glue spraying mechanism 221 and a gluing mechanism 222, wherein the glue spraying mechanism 221 may be used to spray glue on one of surfaces of the bottom layer 202, and the gluing mechanism 222 may be used to bond the surface with glue of the bottom layer with the filler layer. The gluing mechanism 222 comprises a first round roller 2221 and a second round roller 2222, wherein the first round roller 2221 and the second round roller 2222 are tangent, and the filler layer 215 that has undergone hole formation is clamped at the tangent. The second round roller 2222 performs a circular motion to drive the bottom layer 202 that has sprayed with glue, making the bottom layer 202 contact the filler layer 215 at the tangent. The first round roller 2221 performs a circular motion and presses the filler layer 215 and the bottom layer 202 closed at the tangent to make the filler layer 215 and the bottom layer 202 glued.

The spreading device 23 may be selected from spreading devices in prior art. In an embodiment, the spreading device 23 may comprise a storage tank and a roller. The storage tank may be used to store the fillers. A transverse tooth structure may be disposed on surface of the roller. The opening of the storage tank may be adhered to outer edge of the tooth structure so as to make the fillers enter a groove of the tooth structure. When the tooth structure rotates, the fillers may be released from the groove.

More preferably, the horizontal shaking device 24 comprises a first round roller 241 and a second round roller 242, wherein the first round roller 241 and the second round roller 242 are tangent, and the filler layer 201 and the bottom layer 202 having the fillers spread thereon are clamped at the tangent. Lengths of the first round roller 241 and the second round roller 242 are greater than width of the filler layer 201. The first round roller 241 and the second round roller 242 perform linear reciprocating motions along the width direction of the filler layer 201 at same frequency and amplitude. The first round roller 241 and the second round roller 242 both slightly contact the filler layer 201 and the bottom layer 202. When the first round roller 241 and the second round roller 242 make reciprocating motions, the filler layer bonded with the bottom layer and the composite material of the bottom layer may be driven by the frictional force. Movement of the composite material may drive the fillers failing to enter the containing chamber (hole) 216 on the filler layer to enter the containing chamber (hole) during constant motions.

In another embodiment, the sealing device 25 may have same structural composition as the bottom sealing device, comprising a glue spraying mechanism 251 and a gluing mechanism 252, wherein the glue spraying mechanism 251 may be used to spray glue on one of surfaces of the seal layer 203; the gluing mechanism 252 may be used to bond the surface sprayed with glue of the seal layer with the filler layer. The gluing mechanism 252 comprises a first round roller 2521 and a second round roller 2522, wherein the first round roller 2521 and the second round roller 2522 are tangent, and composite structure of the filler layer that is bonded with the bottom layer and has undergone filling and shake may be clamped at the tangent. The second round roller 2522 performs a circular motion to drive the seal layer 203 that has sprayed with glue, making the seal layer 203 contact the filler layer 201 at the tangent. The first round roller 2521 performs a circular motion and presses the filler layer 201 and the seal layer 203 together at the tangent to make the filler layer 201 and the seal layer 203 glued.

In an embodiment, round roller 212, round roller 2222, round roller 242 and round roller 2522 may be active rollers that can actively rotate about their respective centres to provide power for movement of the substrate.

Figure 3:
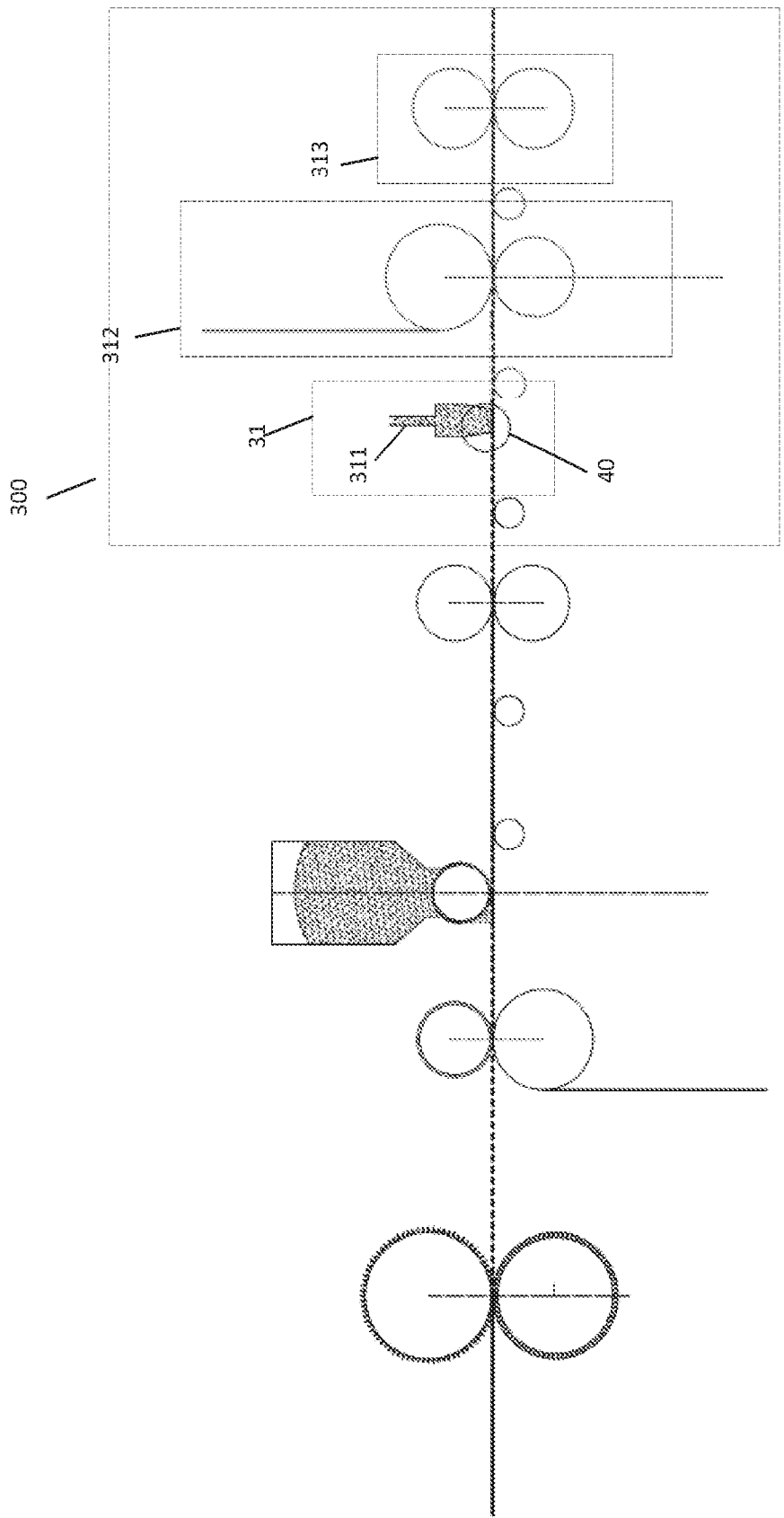
FIG. 3 shows a structure diagram of an producing apparatus performing substrate slit sealing and slitting by hot press slitting or ultrasonic slitting method.
Figure 4:
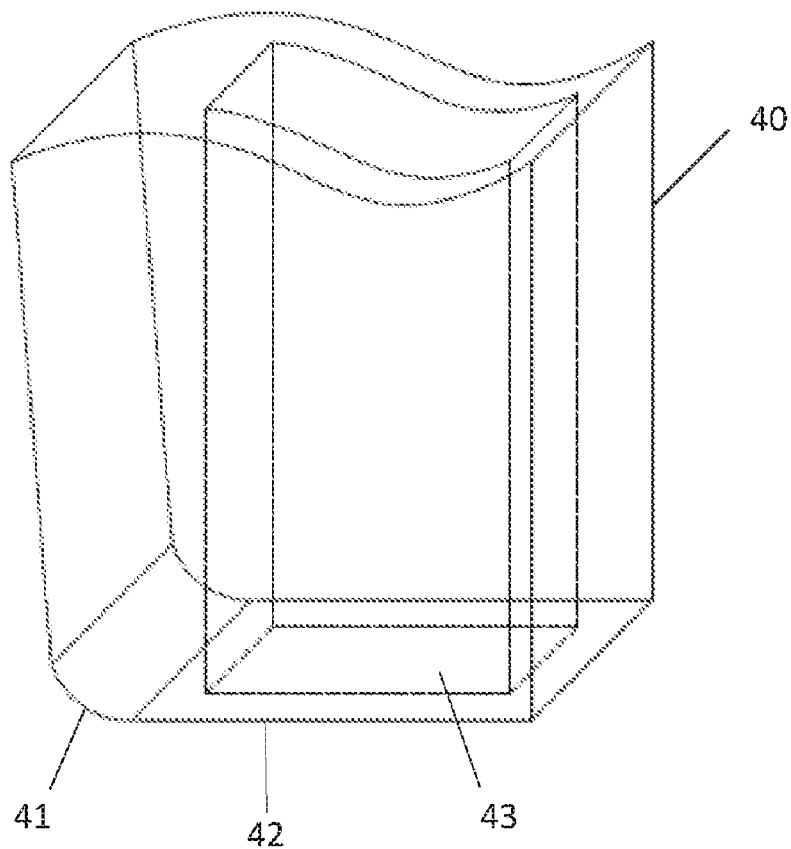
FIG. 4 shows a schematic view of enlarged portion at opening of the absorbing sub-mechanism of the present invention.

In another embodiment, referring to FIG. 3, the sealing device 300 comprises an absorbing mechanism 31, comprising a plurality of absorbing sub-mechanisms 311 that are separate and parallel distributed. Referring to FIG. 4, enlarged portion 40 at opening of the absorbing sub-mechanism 311 is shown in FIG. 4. Bottom of front end of opening of the absorbing sub-mechanism 311 may be in a curved shape 41, and rear end 42 may be straight and close to the filler layer that has undergone horizontal shake. A negative pressure may be generated in the rear end region to form a negative pressure absorbing region 43. The fillers in a plurality of strip regions on the filler layer that has undergone horizontal shake may be sucking removed via the negative pressure absorbing region 43, wherein the strip regions are distributed along the length direction of the filler layer. Since the absorbing mechanism 31 comprises a plurality of separate and parallel distributed absorbing sub-mechanisms 311, the absorbing mechanism 31 may remove the fillers in a plurality of separate strip regions on the filler layer that has undergone horizontal shake, wherein the strip regions are distributed along the length direction of the filler layer, and the strip regions are parallel to each other.

The cross section of the negative pressure absorbing region 43 may be a rectangle, wherein width of the rectangle may be 5 to 25 mm, and length of the rectangle may be 20 to 200 mm. In this embodiment, since continuous suction operation is performed in flow line in the method of the present invention, the length of the suction may be length of the filler layer.

The sealing device 300 further comprises a sealing device 312, having same structural principle as the sealing device 25 of FIG. 2, which may be used to bond the seal layer to surface of the filler layer that has undergone filler suction, to obtain a bonding layer of the seal layer and the filler layer.

The sealing device 300 further comprises a slitting mechanism 313 for slitting the bonding layer along strip regions to obtain the substrate.

As described above, the substrate may be sealed when be slit by a hot knife or an ultrasonic knife. In another preferred embodiment, the slitting mechanism 313 may select pneumatic disc hot knives, using a heating method for slitting. Number of the hot knives may correspond to number of the absorbing sub-mechanisms 311 mentioned above, and position of the hot knives may correspond to position of the absorbing sub-mechanisms 311 to perform slitting operation in filler suction region. The hot knife consists of a flat roller of bottom knife and a set of air pressure disc hot knives. The flat roller and the hot knives are round and can be rotated respectively around their circumferences. Outer circumference of the hot knife may be edged, and the outer circumference of the hot knife may be heated. The edged outer circumference may be tangent to the flat roller of bottom knife, slitting material to be slit at the tangent. Either, ultrasonic knives may be selected, using an ultrasonic method for slitting. Number of the hot knives or the ultrasonic knives may correspond to number of the absorbing sub-mechanisms 311 mentioned above, and position of the hot knives or the ultrasonic knives may correspond to position of the absorbing sub-mechanisms 311 to perform slitting operation in filler suction region, thereby sealing the incision to prevent the fillers from leaking out from the incision.

In order to fill the fillers into the containing chamber (hole) better, technical parameters of frequency and amplitude of the shake performed to the filler layer bonded with the bottom layer and the composite material of the bottom layer may be as follows:

the setting of shaking amplitude A: 3 mm<A<60 mm;
the setting of frequency F: F=K*V/30*L, unit: Hz, indicating number of shake per second,
wherein L may be distance between the spreading device and the sealing device. The usual value of L may be W<L<5W, wherein W may be width of the filler layer. V may be producing speed of raw material substrate, unit: meter/minute. K=frequency coefficient, that is, number of shakes when the raw material runs L/2, generally being 3<K<20. When granular object required to be filled is with great amount and large particle size, while aperture of the containing chamber (hole) is small, the frequency coefficient may be set high, and K≥10 may be taken at this time. On the contrary, when granular object required to be filled is with small amount and small particle size, while aperture of the containing chamber (hole) is large, the frequency coefficient may be set lower, and K≤5 may be taken at this time.

Figure 5:
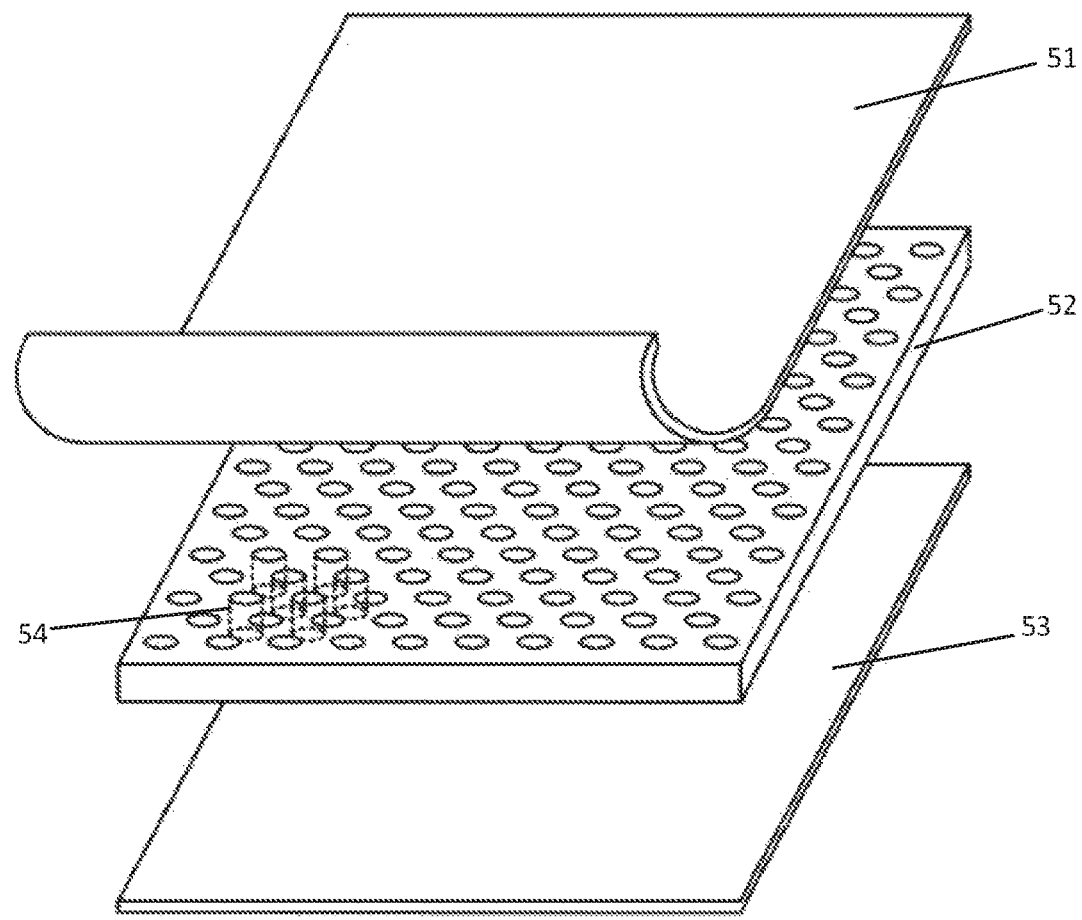
FIG. 5 shows a structure diagram of an embodiment of substrate of the present invention.

The present invention also provides a substrate produced using the method mentioned above. Referring to FIG. 5, the substrate comprises a filler layer 52, a bottom layer 53 and a seal layer 51. The seal layer 51 and the filler layer 52 may be made of a material having liquid permeable function. Through holes may be formed in the filler layer 52. The seal layer 51 and the bottom layer 52 may be sealingly bonded to the filler layer 52 on both sides of the filler layer 52, respectively. The through holes may be filled with fillers. For clarity of illustration, the fillers are not shown in FIG. 5.

The filler may be a water absorber, a water retainer, an anti-inflammatory drug, a disinfectant, an insecticide, a pesticide or a fertilizer, etc. Material of thin substrate may be a non-woven fabric, a polyurethane soft foam rubber, a fibre paper, etc. Thin substrates containing such fillers may be used in a variety of applications such as disposable hygiene products, household health care products and new agricultural products.

Figure 6:
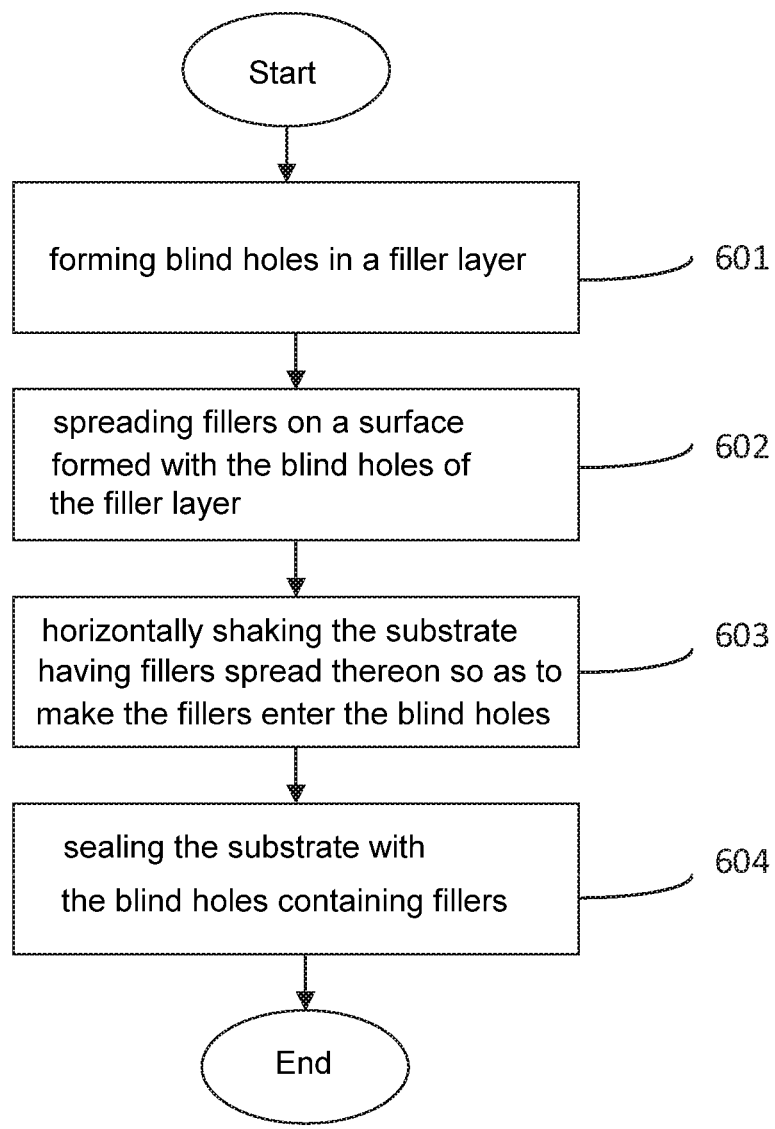
FIG. 6 shows a flow chart of an embodiment of another producing method of the present invention.

In another method for producing filler-containing substrate, features distinguishing to the method mentioned above may be characterized in that blind holes that are not penetrating is provided in the filler layer instead of the through holes provided in the method mentioned above. When sealing the filler layer, only surface formed with the blind holes need to be sealed, but not both sides of the filler layer. Referring to FIG. 6, the method comprises:

601: forming blind holes in a filler layer;
602: spreading fillers on a surface formed with the blind holes of the filler layer;
603: horizontally shaking the substrate having fillers spread thereon so as to make the fillers enter the blind holes;
604: sealing the substrate with the blind holes containing fillers.

Figure 7:
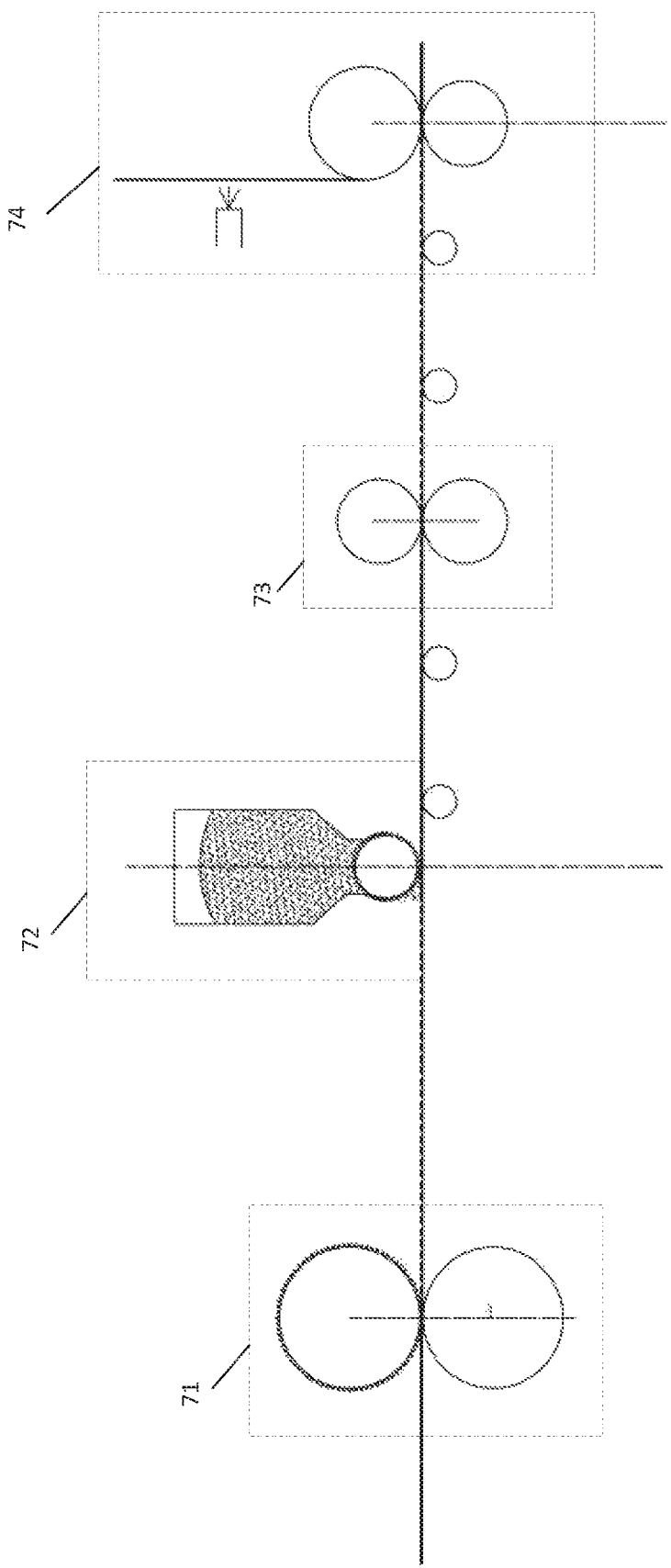
FIG. 7 shows a structure diagram of an embodiment of another producing apparatus of the present invention.

Variations between the producing apparatus corresponding to the producing method shown in FIG. 6 and the producing apparatus shown in FIG. 2 are that production of the blind holes uses a convex roller and a flat roller instead of the needle roller and the concave roller; and there is no bottom layer sealing device. Referring to FIG. 7, the apparatus comprise:

a hole-forming device 71 for forming blind holes in the filler layer;

a spreading device 72 for spreading fillers on the surface formed with the blind holes of the filler layer;

a horizontal shaking device 73 for horizontally shaking the filler layer having the fillers spread thereon so as to allow the fillers to enter the blind holes;

a sealing device 74 for sealing the substrate with the blind holes containing fillers.

Figure 8:
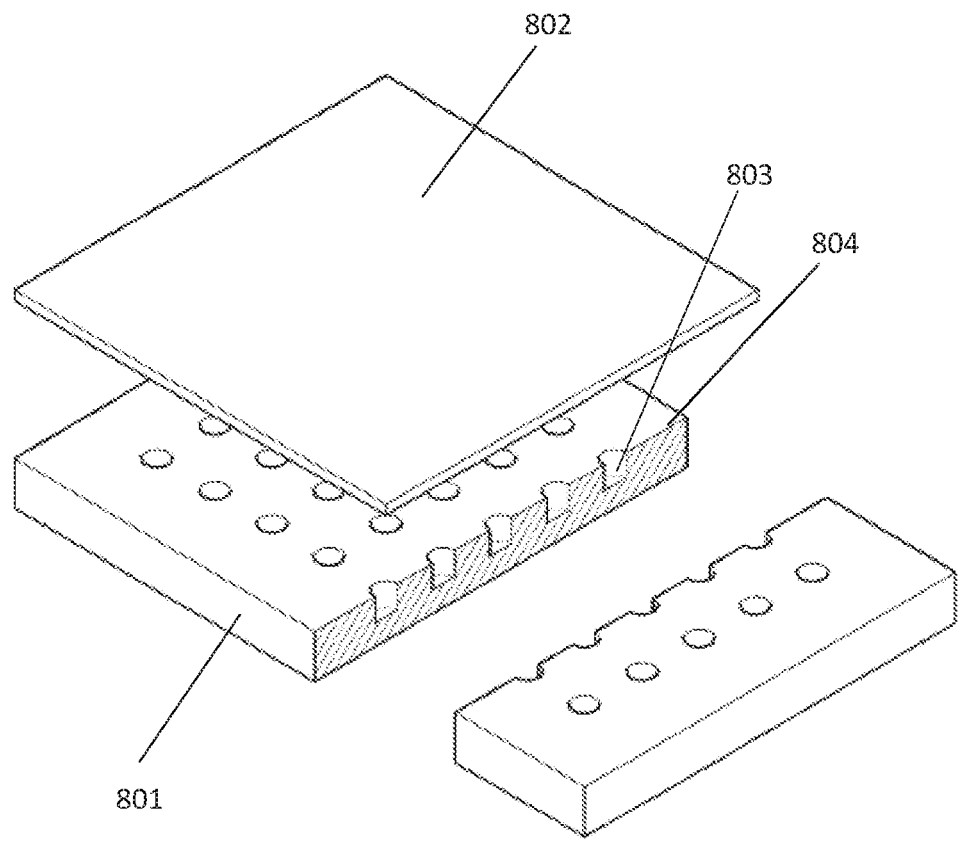
FIG. 8 shows a structure diagram of an embodiment of another substrate of the present invention.

Referring to FIG. 8, corresponding produced substrate may comprise a filler layer 801 and a seal layer 802, wherein the filler layer 801 may be made of a material having liquid permeable function; blind holes 803 may be formed in the filler layer 801; the seal layer 802 may be sealingly bonded with the filler layer 801 on surface 804 formed with blind holes 803 of the filler layer 801; the blind holes 803 may be filled with disinfectants as fillers. For the sake of clarity of illustration, the fillers are not shown in FIG. 8.

The previous description of the disclosure is provided to enable any person skilled in the art to make or use the disclosure. Various modifications to the present disclosure will be obvious to those skilled in the art, and the general principles defined herein may be applied to other variations without departing from the spirit or scope of the disclosure. Thus, the present disclosure is not intended to be limited to the examples and designs described herein, but is to be accorded the broadest scope of the principles and novel features disclosed herein.

What is claimed:

1. An apparatus for producing filler-containing substrate comprising a filler layer and a seal layer, wherein the apparatus comprises:

a hole-forming device for forming holes in the filler layer, the filler layer continuously moving along a length direction of the filler layer;

a spreading device for spreading fillers on a surface formed with the holes of the filler layer that has undergone hole formation;

a horizontal shaking device for horizontally shaking the filler layer having the fillers spread thereon so as to allow the fillers to enter the holes, the horizontally shaking comprises shaking the filler layer along a width direction of the filler layer which is perpendicular to the length direction of the filler layer; and a sealing device for sealing the filler layer having the holes containing the fillers.

2. The apparatus of claim 1, wherein the substrate further comprises a bottom layer, the holes are through holes, the hole-forming device comprises:

a needle roller and a concave roller, wherein surface of the needle roller has needle protrusions;

surface of the concave roller has depressions matching the needle protrusions, the filler layer is placed between the needle roller and the concave roller, wherein the concave roller and the needle roller are heated to 90-250 degrees centigrade, and when the needle protrusions move into the depressions, the through holes are formed on the filler layer; and a bottom layer sealing device for bonding the bottom layer with the surface formed with the holes of the filler layer that has undergone hole formation to cover at least one of the holes.

3. The apparatus of claim 1, wherein the holes are blind holes, the hole-forming device comprises:

a convex roller and a flat roller, wherein surface of the convex roller has flat head protrusions;

the filler layer is placed between the convex roller and the flat roller, wherein the convex roller and the flat roller are heated to 90-250 degrees centigrade, and when the flat head protrusions move to the flat roller, the blind holes are formed on the filler layer.

4. The apparatus of claim 1, wherein the sealing device comprises:

a glue spraying mechanism for spraying glue on a surface of the seal layer;

a gluing mechanism for pressing the surface sprayed with the glue of the seal layer against the surface with the formed holes of the filler layer.

5. The apparatus of claim 1, wherein the apparatus further comprises:

at least two horizontal flattening rollers for holding the filler layer;

wherein the filler layer continuously moves along the length direction of the filler layer on the horizontal flattening rollers.

6. The apparatus of claim 5, wherein the horizontal shaking device comprises:

a first round roller and a second round roller, wherein the first round roller and the second round roller are tangent, and the filler layer having the fillers spread thereon is clamped at the tangent, widths of the first round roller and the second round roller are greater than width of the filler layer, the first round roller and the second round roller perform a linear reciprocating motion along a width direction of the filler layer at same frequency and amplitude.

7. The apparatus of claim 5, wherein the sealing device comprises:

a first round roller and a second round roller, wherein the first round roller and the second round roller are tangent, and the filler layer that has undergone horizontal shake is clamped at the tangent;

a glue spraying mechanism for spraying glue on a surface of the seal layer;

the first round roller performs a circular motion to drive the seal layer that has sprayed with the glue, making the surface sprayed with the glue of the seal layer contact the filler layer at the tangent, the second round roller performs a circular motion and presses the seal layer closed at the tangent to make the filler layer and the seal layer glued.

8. The apparatus of claim 5, wherein the sealing device comprises:

an absorbing mechanism, comprising a plurality of absorbing sub-mechanisms that are separate and parallel distributed, wherein openings of the absorbing sub-mechanisms have a rectangular cross section, width of the rectangular cross section is smaller than width of the filler layer, bottom of front end of the openings is curved, rear end is straight and close to the filler layer that has undergone horizontal shake, a negative pressure is generated in a rear end region, the absorbing mechanism is configured to remove the fillers in a plurality of separate strip regions on the filler layer that has undergone horizontal shake, the strip regions are distributed along a length direction of the filler layer, the strip regions are parallel to each other;

a first round roller and a second round roller, wherein the first round roller and the second round roller are tangent, and the filler layer that has undergone filler absorption in the strip regions is clamped at the tangent;

a glue spraying mechanism for spraying glue on a surface of the seal layer;

the first round roller performs a circular motion to drive the seal layer that has sprayed with the glue, making a surface sprayed with the glue of the seal layer contact a surface formed with the holes of the filler layer at the tangent, the second round roller performs a circular motion and presses the seal layer closed at the tangent so as to make the filler layer and the seal layer glued to obtain a bonding layer of the seal layer and the filler layer;

a slitting mechanism for slitting the bonding layer along the strip regions so as to fuse incision of the bonding layer closed to obtain the substrate.

9. The apparatus of claim 8, wherein the slitting mechanism comprises:
a heat knife, using heating method for slitting; or
an ultrasonic knife, using ultrasonic method for slitting.

10. The apparatus of claim 6, wherein an amplitude is 3-60 mm, a frequency $F=(K*V)/(30*L)$, which is in unit of hertz, the K is a frequency coefficient in a range from 3 to 20, the V is moving speed of the filler layer on the horizontal flattening rollers in unit of m/min, the L is distance between the spreading device and the sealing device in unit of meter, the L is 1-5 times the width of the filler layer.

11. The apparatus of claim 10, wherein value of the K ranges from 3 to 5.

12. The apparatus of claim 10, wherein value of the K ranges from 10 to 20.

* * * * *